United States Patent [19]

Shah et al.

[11] 4,357,318

[45] Nov. 2, 1982

[54] DENTIFRICES WITH IMPROVED SOLUBLE FLUORIDE AVAILABILITY

[75] Inventors: Nutan B. Shah, New Rochelle, N.Y.; Nicholas F. Schmidt, Brookfield, Conn.

[73] Assignee: Richardson-Vicks Inc., Wilton, Conn.

[21] Appl. No.: 288,905

[22] Filed: Jul. 31, 1981

[51] Int. Cl.$^3$ .................................................. A61K 7/18
[52] U.S. Cl. ........................................ 424/52; 424/49; 424/57
[58] Field of Search ...................................... 424/52, 57

[56] References Cited

U.S. PATENT DOCUMENTS

| | | | |
|---|---|---|---|
| 3,119,743 | 1/1964 | Ericsson | 167/93 |
| 3,227,617 | 1/1966 | Manahan et al. | 167/93 |
| 3,227,618 | 1/1966 | Manahan et al. | 167/93 |
| 3,622,662 | 11/1971 | Roberts | 424/54 |
| 3,699,220 | 10/1972 | Weststrate et al. | 424/52 |
| 3,864,471 | 2/1975 | King et al. | 424/52 |
| 3,941,877 | 3/1976 | King et al. | 424/52 |
| 3,956,478 | 5/1976 | King et al. | 424/52 |
| 3,956,480 | 5/1976 | Dichter et al. | 424/49 |
| 4,016,255 | 4/1977 | Forward et al. | 424/52 |
| 4,046,872 | 9/1977 | Mitchell et al. | 424/52 |
| 4,139,599 | 2/1979 | Tomlinson et al. | 424/57 |

*Primary Examiner*—Shep K. Rose
*Attorney, Agent, or Firm*—Salvatore R. Conte

[57] ABSTRACT

Dentifrice preparations having improved soluble fluoride availability are obtained by incorporation of a dibasic alkali metal phosphate either alone or in combination with a calcium ion chelating agent.

27 Claims, No Drawings

DENTIFRICES WITH IMPROVED SOLUBLE FLUORIDE AVAILABILITY

FIELD OF THE INVENTION

This invention relates to dentifrices containing soluble fluoride and is particularly concerned with fluoride-containing dentifrices having calcium carbonate as the abrasive and a water soluble monofluorophosphate salt as the source of available soluble fluoride.

BACKGROUND OF THE INVENTION

It has long been known that treatment of tooth surfaces with fluorides has a caries-inhibiting effect. To obtain this effect, fluoride compounds have been incorporated into dentifrices. However, a dentifrice containing a soluble fluoride and calcium carbonate as the abrasive loses an appreciable amount of available fluorine in the composition upon aging. It has been found that the calcium containing abrasive removes the soluble fluoride from the composition by forming insoluble and inactive calcium fluoride ($CaF_2$), thereby reducing the anticariogenic effectiveness of the fluoride dentifrice.

It is, therefore, an object of this invention to provide dentifrice compositions containing a source of soluble fluoride and calcium carbonate abrasive with improved levels of soluble fluoride availability maintained over a prolonged period of time.

SUMMARY OF THE INVENTION

It has now been surprisingly found that the inactivation of soluble fluoride by calcium carbonate in dentifrices containing a water soluble monoflurophosphate salt as the source of available soluble fluoride may be markedly inhibited by the incorporation of a minor amount of a water soluble dibasic alkali metal phosphate either alone or together with a minor amount of a calcium ion chelator.

DETAILED DESCRIPTION OF THE INVENTION

It has been discovered that the addition of a minor amount of a dibasic alkali metal phosphate to a dentifrice, such as a toothpaste, tooth powder and the like, which contains a water soluble monoflurophosphate salt as the source of soluble fluoride and calcium carbonate as the abrasive component will improve the level of soluble fluoride availability in the dentifrice over a significantly long period of time and reduce the formation of insoluble calcium fluoride.

A soluble monofluorophosphate is the preferred salt over such fluoride salts as, for example, sodium fluoride and stannous fluoride as the fluorine component (source of available soluble fluoride) to be incorporated in calcium carbonate base dentifrices due to its relatively better compatibility with the calcium abrasive. However, the stability of the monofluorophosphate salt is also found to be unacceptable due to the loss of available soluble fluoride in the dentifrice and thus the need for fluoride stabilization arises. The inactivation of available soluble fluoride is mainly caused by the calcium ion content produced by calcium carbonate as the abrasive in the dentifrice composition.

When a soluble monoflurophosphate salt such as sodium monoflurophosphate is dissolved in water it produces free fluoride ion and monofluorophosphate ion in addition to the undissociated sodium monofluorophosphate salt, the three species existing in an equilibrium condition. If fluoride ion is removed from the solution as, for example, by reaction with calcium ion, then more fluoride ion will be formed by ionization of the undissociated sodium monofluorophosphate salt until the equilibrium concentrations are again achieved. At this point, additional calcium ion can react with the reformed fluoride ion and again cause an imbalance in the equilibrium. This cycle can repeat itself until either all the fluoride or calcium ion is exhausted.

To avoid such loss of available soluble fluoride, attempts have been made to inhibit the calcium ion content, for example, by calcium ion chelation utilizing such chelating agents as, for example, ethylenediamine tetraacetic acid or sodium salts thereof in the dentifrice composition (e.g. see our copending application Ser. No. 148,548, filed May 9, 1980). However, the overall stability of the fluoride source is not improved to the extent experienced by the instant invention.

It has been found that the extent and rate of ionization of sodium monofluorophosphate in a calcium carbonate base dentifrice can be suppressed by incorporating a minor amount of a dibasic alkali metal (e.g., sodium, potassium, lithium), phosphate, preferably dibasic sodium phosphate ($Na_2HPO_4$), in the dentifrice, in an amount from about 0.3 to about 1.0 percent by weight based on the total weight of the composition (% w/w). Without being theory-bound, it is believed that in the presence of the dibasic alkali metal phosphate, which acts as a source of phosphate ions, the aforementioned equilibrium will shift to more undissociated sodium monofluorophosphate and less free fluoride ions and monofluorophosphate ions; and, since undissociated sodium monofluorophosphate does not react with calcium ions, better soluble fluoride availability is retained in the calcium carbonate containing dentifrice.

In U.S. Pat. No. 3,622,662, a dentifrice is disclosed with sodium monofluorophosphate as the fluoride source, calcium carbonate as the abrasive, clove or mint oil as the flavoring agent and benzyl alcohol as a gum desensitizer. Due to separation occuring between the flavoring oil and the benzyl alcohol, an alkali metal phosphate having a pKa of at least 7 in water at 25° C. is utilized as a stabilizer to prevent such separation. Neither is it taught nor even suggested, however, that dibasic alkali metal phosphates will maintain high levels of fluoride availability as is shown herein. In any event, the dentifrices of this invention do not utilize benzyl alcohol so that the separation problem noted in said U.S. Pat. No. 3,622,662 is non-existent.

The present invention thus provides a dentifrice composition, particularly a dental cream, comprising a water soluble monofluorophosphate salt as a source of soluble fluoride in a therapeutically effective anti-caries concentration, an effective abrasive amount of calcium carbonate and from about 0.3 to about 1.0 percent by weight of a dibasic alkali metal phosphate, said dentifrice composition being devoid of benzyl alcohol.

It has also been found that a minor amount of a water soluble calcium ion chelator in combination with the dibasic alkali metal phosphate further enhances inhibition of calcium ion inactivation of soluble fluoride. Preferably, from about 0.1 to about 1.0% w/w of the calcium ion chelating agent may be so employed in combination with about 0.3 to about 1.0% w/w of the dibasic alkali metal phosphate. Typical calcium ion chelators employable herein are sodium hexametaphosphate and water-soluble salts of ethylenediamine tetracetic acid such as, for example, di- or tetrasodium ethylenediamine tetraacetate. Other calcium ion chelating agents, e.g., water soluble gluconates, citrates and the like, may also be utilized. The most preferred are sodium hexametaphosphate and tetrasodium ethylenediamine tetraacetate.

In a preferred embodiment of this invention, the dibasic alkali metal phosphate is utilized as the sole component, other than the calcium ion chelator if present, for increasing retention of said soluble monofluorophosphate as fluoride. In another preferred embodiment, calcium carbonate is utilized as the sole abrasive component in addition to said sole utilization of the dibasic alkali metal phosphate.

The preferred source of fluoride in the dentifrice compositions of this invention is a water soluble alkali metal monofluorophosphate salt such as sodium monofluorophosphate, lithium monofluorophosphate and potassium monofluorophosphate, preferably sodium monofluorophosphate. In addition, other monofluorophosphate salts which have sufficient water solubility for use in the dentifrices of the instant invention includes those described in U.S. Pat. No. 4,046,872, for example, ammonium monofluorophosphate, magnesium monofluorophosphate and aluminum monofluorophosphate. In addition, the term "monofluorophosphate" includes water soluble monofluoropolyphosphates such as $Na_4P_3O_9F$, $K_4P_3O_9F$, $(NH_4)_4P_3O_9F$, $Na_3KP_3O_9F$, $(NH_4)_3NaP_3O_9F$ and $Li_4P_3O_9F$.

The fluoride component will generally be present in the dentifrice compositions in an amount of from about 0.1 to about 5.0 weight percent based on the total weight of the composition and preferably in an amount of from about 0.5 to about 1% and most preferably in an amount of from about 0.75 to about 0.85% by weight.

Any suitable surface active or detersive material may be included in the dentifrice compositions. Such compatible materials are desirable to provide additional detersive, foaming and anti-bacterial properties depending upon the specific type of surface active material. These detergents are usually water-soluble organic compounds and may be anionic nonionic or cationic in structure. It is usually preferred to use the water-soluble non-soap or synthetic organic detergents. Suitable detersive materials are known and include, for example, the water-soluble salts of higher fatty acid monoglyceride monosulfate detergents (e.g. sodium coconut fatty acid monoglyceride monosulfate), higher alkyl sulfate (e.g. sodium lauryl sulfate), alkyl aryl sulfonate (e.g., sodium dodecyl benzene sulfonate), higher fatty acid esters of 1,2-dihydroxy propane sulfonate (e.g. sodium coconut fatty acid ster of 1,2-dihydroxy propane sulfonate), and the like. The various surface active materials may be used in any suitable amount, generally from about 0.05 to about 10 percent by weight, and preferably from about 0.5 to 5 percent by weight of the dentifrice composition.

In dental cream formulations, the liquids and solids should be proportioned to form an extrudable creamy mass of desirable consistency. In general, liquids in the dental cream will comprise chiefly water, glycerin, sorbitol, propylene glycol, or the like, including suitable mixtures thereof. It is advantageous usually to use a mixture of both water and a humectant or binder such as glycerin or sorbitol. It is preferred to use glycerin. The total liquid content will generally be about 20 to 75 percent by weight of the formulation. It is also preferred to use a gelling agent in dental creams such as the natural and synthetic gum and gum-like material, e.g. Irish moss, gum tragacanth, xanthan gum, Veegum regular, sodium carboxymethylcellulose, polyvinylpyrrolidone, starch, and the like. The Irish moss and sodium carboxymethylcellulose are compatible particularly and are preferred gelling agents. The gum content is usually in an amount up to about 10 percent and preferably about 0.5 to 5 percent by weight of the formulation.

Various other materials may be incorporated as adjuvants in the dentifrice preparations of this invention. Examples thereof are coloring or whitening agents, preservatives, silicones, chlorophyll compounds, ammoniated materials such as urea, diammoniumphosphate and mixtures thereof, and other constitutents. A small amount of colloidal silica, for example, is often incorporated into toothpaste formulations as a thickener, giving some body to the formulation upon swelling when in contact with water. The foregoing adjuvants are suitably selected and incorporated in the instant compositions in amounts which do not substantially adversely affect the properties and characteristics desired for the particular type of composition.

For some purposes it may be desirable to include antibacterial agents in the compositions of the present invention. Typical antibacterial agents which may be used in amounts of about 0.01 percent to about 5 percent, preferably about 0.05 percent to about 1.0 percent, by weight of the dentifrice composition include: $N^1$-(4-chlorobenzyl)-$N^5$-(2,4-dichlorobenzyl)biguanide, p-chlorophenyl biguanide, 4-chlorobenzhydryl biguanide, 4-chlorobenzhydrylguanylurea, N-3-lauroxpropyl-$N^5$-p-chlorobenzylbiguanide, 1,6-di-p-chlorophenyl-biguanidohexane, 1-(lauryldimethylammonium)-8-(p-chlorobenzyldimethlyammonium)octane dichloride, 5,6-dichloro-2-guanidinobenzimidazole, $N^1$-p-chlorophenyl-$N^5$-laurylbiguanide, 5-amino-1,3-bis(2-ethylexyl)-5-methylhexahydropyrimidine, and their non-toxic acid addition salts.

Tooth desensitization agents such as, for example, a nitrate of potassium lithium or sodium disclosed in U.S. Pat. No. 3,863,006 issued Jan. 28, 1975 to Milton Hodosh, may also be incorporated in the dentifrice compositions in tooth desensitizing amounts, generally up to about 20% and preferably about 5% by weight.

Any suitable flavoring or sweetening materials may be employed in formulating a flavor for the compositions of the present invention. Examples of suitable flavoring constituents include the flavoring oils, e.g. oils of spearmint, peppermint, wintergreen, sassafras, clove, sage, eucalyptus marjoram, cinnamon, lemon and orange, as well as sodium methylsalicylate. Suitable sweetening agents include sucrose, lactose, maltose, sorbitol, sodium cyclamate, ammonium glycyrrhizinate and its derivatives and saccharin. Suitably, flavor and sweetening agent may together comprise from about 0.01 to 5 percent or more of the compositions of the instant invention.

The dental cream should have a pH practicable for use. A neutral to basic pH is particularly desirable. The initial pH range of about 7 to 9.5 perferably 7.5, is considered the most practicable for use. Such pH determination is made on a 10% aqueous suspension of the dentifrice. If necessary, conventional basic materials may be added to adjust the pH as desired.

The dentifrice compositions of this invention are prepared in the conventional manner of making dental creams, tooth powders, etc. In general, the dibasic alkali metal phosphate, e.g. dibasic sodium phosphate, either alone or in combination with the calcium ion chelator, e.g. sodium hexametaphosphate or tetrasodium ethylenediamine tetraacetate, is preferably added to the formulation containing the calcium carbonate abrasive prior to the incorporation of the fluoride component e.g., sodium monofluorophosphate, in order to tie up free calcium ions prior to the incorporation of the fluoride component.

It has been found that dentifrice compositions of this invention maintain substantially higher levels of soluble fluoride and for longer periods than similar compositions without the dibasic alkali metal phosphate, either alone or in combination with a calcium ion chelator, as provided for herein.

The following specific examples are further illustrative of the nature of the present invention, but it is to be understood that the invention is not limited thereto. All amounts of the various ingredients are by weight unless otherwise specified.

EXAMPLE 1

The following typifies a basic formulation for a fluoride dental cream with calcium carbonate as the abrasive and sodium monofluorophosphate as the source of soluble fluoride.

| Base Formula No.1 | | |
|---|---|---|
| Ingredients | % w/w | Grams |
| Glycerin | 12.25 | 980.0 |
| Sodium carboxymethylcellulose | 0.92 | 73.6 |
| Xanthan gum | 0.38 | 30.4 |
| Sodium saccharin | 0.23 | 18.4 |
| Methylparaben | 0.06 | 4.8 |
| Propylparaben | 0.02 | 1.6 |
| Sorbitol solution (70% w/v) | 9.00 | 720.0 |
| Potassium nitrate | 5.00 | 400.0 |
| Sodium lauryl sulfate | 2.10 | 168.0 |
| Colloidal silica | 1.00 | 80.0 |
| Calcium carbonate | 30.00 | 2400.0 |
| Flavoring | 1.35 | 108.0 |
| Sodium monofluorophosphate | 0.81 | 64.8 |
| Distilled water, to make | 100.00 | 8000.0 |

The sodium carboxymethylcellulose, xanthan gum, sodium saccharin and parabens are mixed and dispersed in the glycerin. The sorbitol is mixed with about 1800 grams water and the glycerin mixture added to it. The potassium nitrate, dissolved in about 730 grams water with heating, is then added. The three powders (sodium lauryl sulfate, calcium carbonate and colloidal silica) are mixed in at high speed under vacuum and flavoring then added. Finally, a solution of the sodium monofluorophosphate dissolved in the remaining water is added. The amount of sodium monofluorophosphate slightly exceeds the desired theoretical fluoride content of 1000 ppm (equal to 0.76%, w/w).

EXAMPLE 2

To Base Formula No. 1, described in Example 1, is added 1.0% w/w (80.0 grams) of anhydrous sodium phosphate dibasic ($Na_2HPO_4$). With reference to the order of admixture described in Example 1, a solution of the sodium phosphate dissolved in sufficient water is incorporated into the dental cream mixture prior to the addition step of the calcium carbonate abrasive. Both the Base Formula No. 1 (control) and the instant sodium phosphate containing composition are aged at 25°, 37° and 45° C., respectively, and the amount of total soluble fluoride is determined periodically in parts per million (ppm) by standard measurement. The results are indicated in the table below. Although each composition is formulated to contain at least a theoretical 1000 ppm of total soluble fluoride, the lower initial measurement is deemed due to unavoidable loss upon first contact with calcium ion during admixture.

| | Base Formula No. 1 | |
|---|---|---|
| Temperature (°C.) versus Time (months) | Without $Na_2HPO_4$ | With 1% $Na_2HPO_4$ |
| | (ppm) | (ppm) |
| 25°/Initial | 900 | 960 |
| 25°/3 mo. | 670 | 820 |
| 25°/6 mo. | * | 710 |
| 37°/1 mo. | 630 | 790 |
| 37°/2 mo. | * | 720 |
| 37°/3 mo. | 420 | 680 |
| 45°/1 mo. | 540 | 690 |
| 45°/2 mo. | * | 640 |
| 45°/3 mo. | 340 | 580 |

*indicates no measurement taken.

EXAMPLE 3

A fluoride toothpaste containing 1% w/w dibasic sodium phospate was prepared formulated as follows:

| Ingredients | % w/w | Grams |
|---|---|---|
| Glycerin | 12.50 | 1000.0 |
| Sodium carboxymethylcellulose | 0.20 | 16.0 |
| Xanthan gum | 0.55 | 44.0 |
| Sodium saccharin | 0.20 | 16.0 |
| Methylparaben | 0.06 | 4.8 |
| Propylparaben | 0.02 | 1.6 |
| Sorbitol solution (70% w/v) | 12.50 | 1000.0 |
| Anhy. sodium phosphate dibasic | 1.00 | 80.0 |
| Colloidal silica | 1.70 | 136.0 |
| Calcium carbonate | 35.00 | 2800.0 |
| Sodium lauryl sulfate | 1.50 | 120.0 |
| Alcohol U.S.P. | 0.50 | 40.0 |
| Flavoring | 1.40 | 112.0 |
| Sodium monofluorophosphate | 0.82 | 65.6 |
| Distilled water, to make | 100.00 | 8000.0 |

To the first six ingredients, mixed together as in Example 1, is incorporated an aqueous solution of the sodium phosphate. The colloidal silica and calcium carbonate are combined and added to the mixture at high speed under vacuum. The sodium lauryl sulfate, alcohol and flavoring are combined and added. Finally, an aqueous solution of the sodium monofluorophosphate is added and the entire composition thoroughly mixed. As in Example 2, the amount of total soluble fluoride (ppm) is determined periodically:

| °C./Months | Available Fluoride (ppm) |
|---|---|
| 25°/Initial | 970 |
| 25°/3 mos. | 900 |
| 25°/6 mos. | * |
| 37°/1 mo. | * |
| 37°/2 mos. | 740 |
| 37°/3 mos. | 690 |
| 45°/1 mo. | * |
| 45°/2 mos. | 690 |
| 45°/3 mos. | 620 |

EXAMPLE 4

Two dental creams are prepared according to the Basic Formula of Example 1 except that in one 0.3% by weight of sodium hexametaphosphate (NaHMP) is incorporated (control) and in the other 1.0% by weight of dibasic sodium phosphate plus 0.3% by weight of sodium hexametaphosphate is incorporated. Periodic determinations of total fluoride availability yield the following data.

| | Soluble Fluoride (ppm) | |
|---|---|---|
| °C./Months | With 0.3% NaHMP | With 1.0% $Na_2HPO_4$ and 0.3% NaHMP |
| 25°/Initial | 910 | 910 |
| 25°/3 mos. | 760 | * |
| 25°/6 mos. | * | 840 |
| 37°/1 mo. | 730 | 800 |
| 37°/2 mos. | * | 710 |
| 37°/3 mos. | 490 | 680 |
| 45°/1 mo. | 640 | 740 |
| 45°/2 mos. | * | 620 |
| 45°/3 mos. | 370 | * |

EXAMPLE 5

Two dental creams are prepared according to the Basic Formula of Example 1 except that in one 0.3% by weight of tetrasodium ethylenediamine tetraacetate (NaEDTA) is incorporated (control) and in the other 1.0% by weight of dibasic sodium phosphate plus 0.3% by weight of tetrasodium ethylenediamine tetraacetate is incorporated. Periodic determinations of total fluoride availability yield the following data:

| | Soluble Fluoride (ppm) | |
|---|---|---|
| °C./Months | With 0.3% NaEDTA | With 1.0% $Na_2HPO_4$ and 0.3% NaEDTA |
| 25°/Initial | 910 | 910 |
| 25°/3 mos. | 690 | 870 |
| 25°/6 mos. | * | * |
| 37°/1 mo. | 650 | 770 |
| 37°/2 mos. | * | 710 |
| 37°/3 mos. | 440 | 680 |
| 45°/1 mo. | 570 | 730 |
| 45°/2 mos. | * | 670 |
| 45°/3 mos. | 350 | 600 |

The foregoing Examples demonstrate the marked improvement in increasing the retention of fluoride availability with compositions of this invention. In Examples 1–3, for instance, addition of 1% w/w dibasic sodium phosphate to standard toothpaste formulations is shown to provide exceptional fluoride availability over an interval of several months at both ambient (25° C.) and elevated (35° C.; 45° C.) temperatures. It is particularly noteworthy that the inclusion of dibasic sodium phosphate provided fluoride levels (measured in parts per million) far in excess of 600 ppm after 3 months at 37° C. In contrast, the fluoride level measured only 420 ppm in the absence of dibasic sodium phosphate.

This is a significant finding since, as a rule, if a dentifrice composition shows more than 600 ppm available fluoride after storage at 37° C. for three months, it can be assumed that the composition has a probable shelf-like (ambient temperatures) of three years with retention of at least 600 ppm available fluoride. This shelf-like standard has been considered as a guideline by the OTC Review Panel on Dentifrices and Dental Care Agents for sodium monofluorophosphate dentifrices. It is believed that the subject compositions are the first to meet such standard.

The use of a calcium ion chelator, e.g., sodium hexametaphosphate (NaHMP) in the dentifrice of Example 4 and a water soluble alkali metal salt of ethylenediamine tetraacetic acid such as tetrasodium ethylenediamine tetraacetate (NaEDTA) in the dentifrice of Example 5, in conjunction with dibasic sodium phosphate also yields a marked improvement in increased retention of available soluble fluoride. When, for example, the chelating agent is used alone, a rapid loss of available fluoride occurs and, at elevated temperatures, e.g., 37° C., the fluoride level after 3 months is well below the aforementioned minimum of 600 ppm standard. In contrast, the combined use of dibasic sodium phosphate and the chelating agent provides significantly higher levels than 600 ppm of available fluoride.

We claim:

1. A dentifrice comprising a water soluble monofluorophosphate salt as a source of soluble fluoride in a therapeutically effective anti-caries concentration, an effective abrasive amount of calcium carbonate and from about 0.3 to about 1.0 percent by weight of a dibasic alkali metal phosphate, said dentifrice being devoid of benzyl alcohol.

2. The dentifrice of claim 1 wherein said monofluorophosphate salt is sodium monofluorophosphate.

3. The dentifrice of claim 1 wherein said dibasic alkali metal phosphate is dibasic sodium phosphate.

4. A dentifrice comprising a water soluble monofluorophosphate salt as a source of soluble fluoride in a therapeutically effective anti-caries concentration, an effective abrasive amount of calcium carbonate, from about 0.3 to about 1.0 percent by weight of a dibasic alkali metal phosphate and from about 0.1 to about 1.0 percent by weight of a calcium ion chelator, said dentifrice being devoid of benzyl alcohol.

5. The dentifrice of claim 4 wherein said monofluorophosphate salt is sodium monofluorophosphate and said dibasic alkali metal phosphate is dibasic sodium phosphate.

6. The dentifrice of claim 4 wherein said calcium ion chelator is sodium hexametaphosphate or tetrasodium ethylenediamine tetraacetate.

7. A dentifrice comprising a water soluble monofluorophosphate salt as a source of soluble fluoride in a therapeutically effective anti-caries concentration, an effective abrasive amount of calcium carbonate, and, as the sole component for increasing retention of said monofluorophosphte as a source of soluble fluoride, from about 0.3 to about 1.0 percent by weight of a dibasic alkali metal phosphate, said dentifrice being devoid of benzyl alcohol.

8. The dentifrice of claim 7 wherein said monofluorophosphate salt is sodium monofluorophosphate.

9. The dentifrice of claim 7 wherein said dibasic alkali metal phosphate is dibasic sodium phosphate.

10. The dentifrice of claim 7 to which is added from about 0.1 to about 1.0 percent by weight of a calcium ion chelator.

11. The dentifrice of claim 7 to which is added from about 0.1 to about 1.0 percent by weight of sodium hexametaphosphate or tetrasodium ethylenediamine tetraacetate.

12. A dentifrice comprising a water soluble monofluorophosphate salt as a source of soluble fluoride in a therapeutically effective anti-caries concentration, an effective amount of an abrasive consisting of calcium carbonate and from about 0.3 to about 1.0 percent by weight of a dibasic alkali metal phosphate as the sole component for increasing retention of said monofluorophosphate as a source of soluble fluoride, said dentifrice being devoid of benzyl alcohol.

13. The dentifrice of claim 12 wherein said monofluorophosphate salt is an alkali metal monofluorophosphate.

14. The dentifrice of claim 12 wherein said monofluorophosphate salt is sodium monofluorophosphate.

15. The dentifrice of claim 12 wherein said dibasic alkali metal phosphate salt is dibasic sodium phosphate.

16. A dentifrice comprising sodium monofluorophosphate as a source of soluble fluoride in a therapeutically effective anti-caries concentration, an effective amount of an abrasive consisting of calcium carbonate and from about 0.3 to about 1.0 percent by weight of a dibasic sodium phosphate as the sole component for increasing retention of said monofluorophosphate as a source of soluble fluoride, said dentifrice being devoid of benzyl alcohol.

17. A dentifrice comprising a water soluble monofluorophosphate salt as a source of soluble fluoride in a therapeutically effective anti-caries concentration, an effective amount of an abrasive consisting of calcium carbonate, from about 0.1 to about 1.0 percent by weight of a calcium ion chelator and from about 0.3 to about 1.0 percent by weight of a dibasic alkali metal phosphate as the sole component, other than said calcium ion chelator, for increasing retention of said monofluorophosphate as a source of soluble fluoride, said dentifrice being devoid of benzyl alcohol.

18. The dentifrice of claim 17 wherein said monofluorophosphate salt is an alkali metal monofluorophosphate.

19. The dentifrice of claim 17 wherein said monofluorophosphate salt is sodium monofluorophosphate.

20. The dentifrice of claim 17 wherein said dibasic alkali metal phosphate is dibasic sodium phosphate.

21. The dentifrice of claim 17 wherein said calcium ion chelator is sodium hexametaphosphate.

22. The dentifrice of claim 17 wherein said calcium ion chelator is a water soluble salt of ethylenediamine tetraacetic acid.

23. The dentifrice of claim 17 wherein said calcium ion chelator is tetrasodium ethylenediamine tetraacetate.

24. A dental cream comprising sodium monofluorophosphate as a source of soluble fluoride in a therapeutically effective anti-caries concentration, an effective amount of an abrasive consisting of calcium carbonate, from about 0.1 to about 1.0 percent by weight of sodium hexametaphosphate and from about 0.3 to about 1.0 percent by weight of dibasic sodium phosphate as the sole component, other than said sodium hexametaphosphate, for increasing retention of said sodium monofluorophosphate as a source of soluble fluoride, said dentifrice being devoid of benzyl alcohol.

25. A dental cream comprising sodium monofluorophosphate as a source of soluble fluoride in a therapeutically effective anti-caries concentration, an effective amount of an abrasive consisting of calcium carbonate, from about 0.1 to about 1.0 percent by weight of tetrasodium ethylenediamine tetraacetate and from about 0.3 to about 1.0 percent by weight of dibasic sodium phosphate as the sole component, other than said tetrasodium ethylenediamine tetraacetate, for increasing retention of said sodium monofluorophosphate as a source of soluble fluoride, said dentifrice being devoid of benzyl alcohol.

26. A dental cream consisting essentially of:

| Ingredients | % w/w |
|---|---|
| Anhydrous dibasic sodium phosphate | 1.00 |
| Sodium monofluorophosphate | 0.81 |
| Glycerin | 12.25 |
| Sodium carboxymethylcellulose | 0.92 |
| Xanthan gum | 0.38 |
| Sodium saccharin | 0.23 |
| Methylparaben | 0.06 |
| Propylparaben | 0.02 |
| Sorbitol solution (70% w/v) | 9.00 |
| Potassium nitrate | 5.00 |
| Sodium lauryl sulfate | 2.10 |
| Colloidal silica | 1.00 |
| Calcium carbonate | 30.00 |
| Flavoring | 1.35 |
| Distilled water, to make | 100.00 |

27. A dental cream consisting essentially of:

| Ingredients | % w/w |
|---|---|
| Anhydrous dibasic sodium phosphate | 1.00 |
| Sodium monofluorophosphate | 0.82 |
| Glycerin | 12.50 |
| Sodium carboxymethylcellulose | 0.20 |
| Xanthan gum | 0.55 |
| Sodium saccharin | 0.20 |
| Methylparaben | 0.06 |
| Propylparaben | 0.02 |
| Sorbitol solution (70% w/v) | 12.50 |
| Colloidal silica | 1.70 |
| Calcium carbonate | 35.00 |
| Sodium lauryl sulfate | 1.50 |
| Alcohol U.S.P. | 0.50 |
| Flavoring | 1.40 |
| Distilled water, to make | 100.00 |

* * * * *